US006566646B1

(12) United States Patent
Iwakawa

(10) Patent No.: US 6,566,646 B1
(45) Date of Patent: May 20, 2003

(54) IMAGE INPUT APPARATUS FOR READING CONVEYED ITEMS USING AIR FLOW COOLING OF ILLUMINATION WINDOWS

(75) Inventor: Masato Iwakawa, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 09/528,512

(22) Filed: Mar. 17, 2000

(30) Foreign Application Priority Data

Mar. 18, 1999 (JP) .......................................... 11-073966

(51) Int. Cl.[7] ............................ G06M 7/00; H01J 40/14

(52) U.S. Cl. .................. 250/223 R; 235/375; 209/584; 209/587

(58) Field of Search ...................... 250/223 R; 235/454, 235/375; 209/584, 587, 577, 938, 939

(56) References Cited

U.S. PATENT DOCUMENTS

| | | | | |
|---|---|---|---|---|
| 4,669,865 A | * | 6/1987 | Bessho et al. | 355/30 |
| 5,308,960 A | * | 5/1994 | Smith et al. | 235/454 |
| 5,521,365 A | * | 5/1996 | Malatesta | 235/454 |
| 5,814,802 A | | 9/1998 | Hecht et al. | 235/455 |
| 5,959,669 A | * | 9/1999 | Mizoguchi et al. | 348/362 |

* cited by examiner

*Primary Examiner*—Stephone B. Allen
*Assistant Examiner*—Eric J Spears
(74) *Attorney, Agent, or Firm*—Foley & Lardner

(57) ABSTRACT

The image input apparatus picks up the image of the object moved in the predetermined direction by the conveying means and illuminated by illuminating means having an light source, an internal window glass and an outermost window glass. The internal window glass serves as a heat ray absorbing glass, and an outermost window glass serves as a heat ray transmitting glass. The image input apparatus comprises the air cooling means for generating an air flow to forcedly cool the front and the rear surface of the internal window glass.

8 Claims, 9 Drawing Sheets

CONVEYOR BELT 1
1
4
2 MAIL ITEM
14 IMAGE PICKUP FIELD
15 CAMERA OPTICAL AXIS
4 ILLUMINATING UNIT
209 CONVEYING DIRECTION
PHOTOELECTRIC SENSOR 3
POWER SOURCE UNIT 6
MOUNTING RACK 10
RECOGNIZING UNIT 13
1.5m/s
9 ROTARY ENCODER
8 DUCT
5 CAMERA UNIT
7 AIR FEED UNIT

IMAGE INPUT APPARATUS FOR READING CONVEYED ITEMS USING AIR FLOW COOLING OF ILLUMINATION WINDOWS

BACKGROUND OF THE INVENTION

1. Field of the Invention

The present invention relates to an image input apparatus and, more particularly, to an image input apparatus for illuminating a mail item by an illuminating light source and inputting an image of the illuminated portion in order to sort the mail items by image recognition.

2. Description of the Related Art

Conventionally, as the above-mentioned image input apparatus, there has been provided an apparatus for sorting mail items which are generally called flat mails, (referred to as a flat mail sorter, hereinafter). The size of flat mail is maximum 50 mm in thickness, 400 mm in length, and 300 mm in width, roughly. The flat mail sorter captures an image of a flat mail surface by the image input apparatus, reads a written address by a recognition processing unit existing at the post stage, and sorts and accommodates the mails into a sorting box in which the mail is sorted by district in accordance with the reading result.

The flat mail has physical features that the thickness of the flat mail has a wider range, the lateral width thereof is wider, and the like, as compared with those of a letter (post card, or standard-size mail item, etc.). Therefore, the illumination for the image input requires linear illumination having a wider irradiating-width and a deeper irradiating-depth. This results in necessitating an illuminating light source having a high illuminance and results in generating a large amount of heat.

Since a high output lamp is used for the above reasons in the image input apparatus, an infrared light component of the illuminating light source makes an illuminating window glass, through which irradiated light is transmitted, apt to have a high temperature. As a result, problems readily occur such that light distribution of the illuminating light is degraded and made non-uniform by dust burned onto the window glass, which is generated by mail conveyance, etc., thereby degrading image quality and diminishing sorting performance. This requires frequent maintenance, such as cleaning the illuminating window glass every day. Consequently, for purpose of improvement in maintenance performance, it is necessary to suppress an increase in temperature of the illuminating window glass and decrease dirty region due to the burned dust.

It is necessary to cool the apparatus up to about room temperature before starting a lamp exchanging operation, when lamp burnout occurs. It takes a long time to cool the apparatus due to the usage of the high output lamp on the basis of the above reason, thereby interrupting the operation on the apparatus during the cooling time.

To solve the problems, for example, U.S. Pat. No. 5,814, 802 disclosed an image input apparatus for carrying, along a conveyor, a flat mail onto which a bar code label is put, illuminating the flat mail from the upper side, and detecting an image of the bar code label by a CCD camera, wherein heatsink fins are mounted to a surface on the upper side of a reflective mirror provided in the illuminating means to cover the upper portion of a lamp in the illuminating means, and the illuminating means is cooled by a laminar air flow which flows across the upper portion of the heatsink fins and is exhausted to the outside. However, in this conventional image input apparatus, the heat removal is also insufficiently effected in an area on the conveyor side of the illuminating means and the illuminating window glass is apt to have a high temperature.

SUMMARY OF THE INVENTION

It is an object of the present invention to provide an image input apparatus for a mail item having an illuminating apparatus in which it is difficult for a foreign matter to be burned onto a glass illumination window even if mail items are contacted thereto for a long time. This makes the maintenance simple, and the reliability is excellent.

According to the present invention, there is provided an image input apparatus comprising: illuminating means for irradiating light to an object which conveying means moves in a predetermined direction; image pickup means for picking up an image of the object in a image pickup field; and air cooling means for cooling the illuminating means, wherein the illuminating means has a plurality of window glasses for transmitting irradiated light, among which the outermost window glass is a heat ray transmitting glass and an internal window glass is a heat ray absorbing glass, and the heat ray absorbing glass is forcedly cooled in the front surface and the rear surface thereof by an air flow generated by the air cooling means.

According to the present invention, the internal heat ray absorbing glass absorbs a heat dissipating energy from a light source, and the forced air-cooling operation causes the temperature of the heat ray absorbing glass to decrease, thereby reducing secondary dissipation of a heat dissipating energy from the glass itself as much as possible. The outermost window glass is set to the heat ray transmitting glass. As a consequence, it is capable of preventing the temperature increase of the outermost glass that is caused by the heat dissipating energy, and it is difficult that a foreign matter is burn to the window glass for illumination if being adhered thereto for long time. This makes the maintenance simple, and the reliability to the image input apparatus can be improved.

DETAILED DESCRIPTION OF THE PREFERRED EMBODIMENTS

An embodiment of the present invention will be now described in detail with reference to the drawings.

The construction of the first embodiment will be explained with reference to the drawings.

Figure 1:
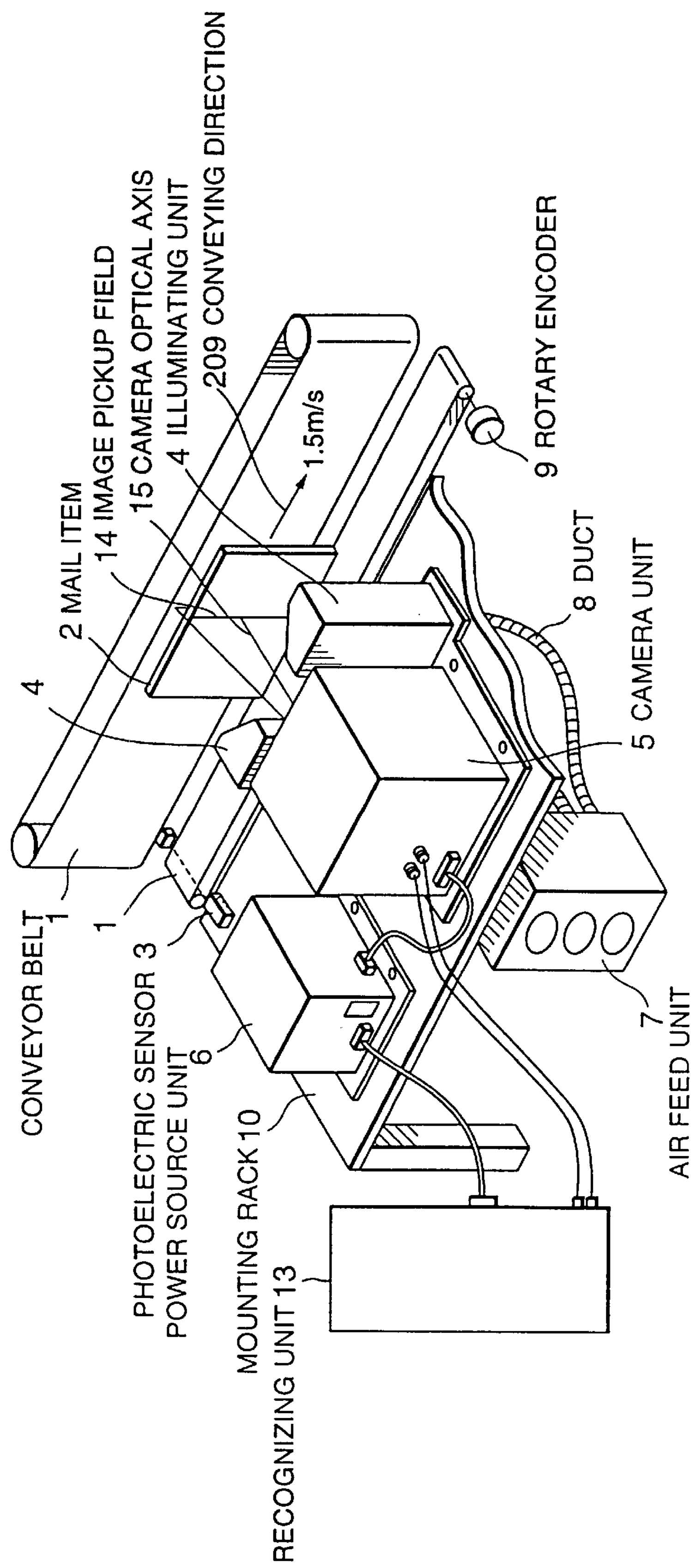
FIG. 1 is a perspective view showing a schematic construction according to a first embodiment of the present invention.

Referring to FIG. 1, a mail item 2 is moved at a predetermined speed, being loaded on a conveyor belt 1.

A photoelectric sensor 3 detects the passage of the mail item 2, and a detected signal is outputted to a recognizing unit 13 through a power source unit 6.

A rotary encoder 9 generates a pulse having a period proportional to a speed of the conveyor belt 1, and outputs the pulse to the power source unit 6.

An air flow feed unit 7 feeds air for air-cooling to illuminating units 4 and a camera unit 5.

The illuminating units 4 illuminate the mail item 2 linearly. Two illuminating units 4 are provided, sandwiching a image pickup field 14 of camera unit 5.

Figure 2:
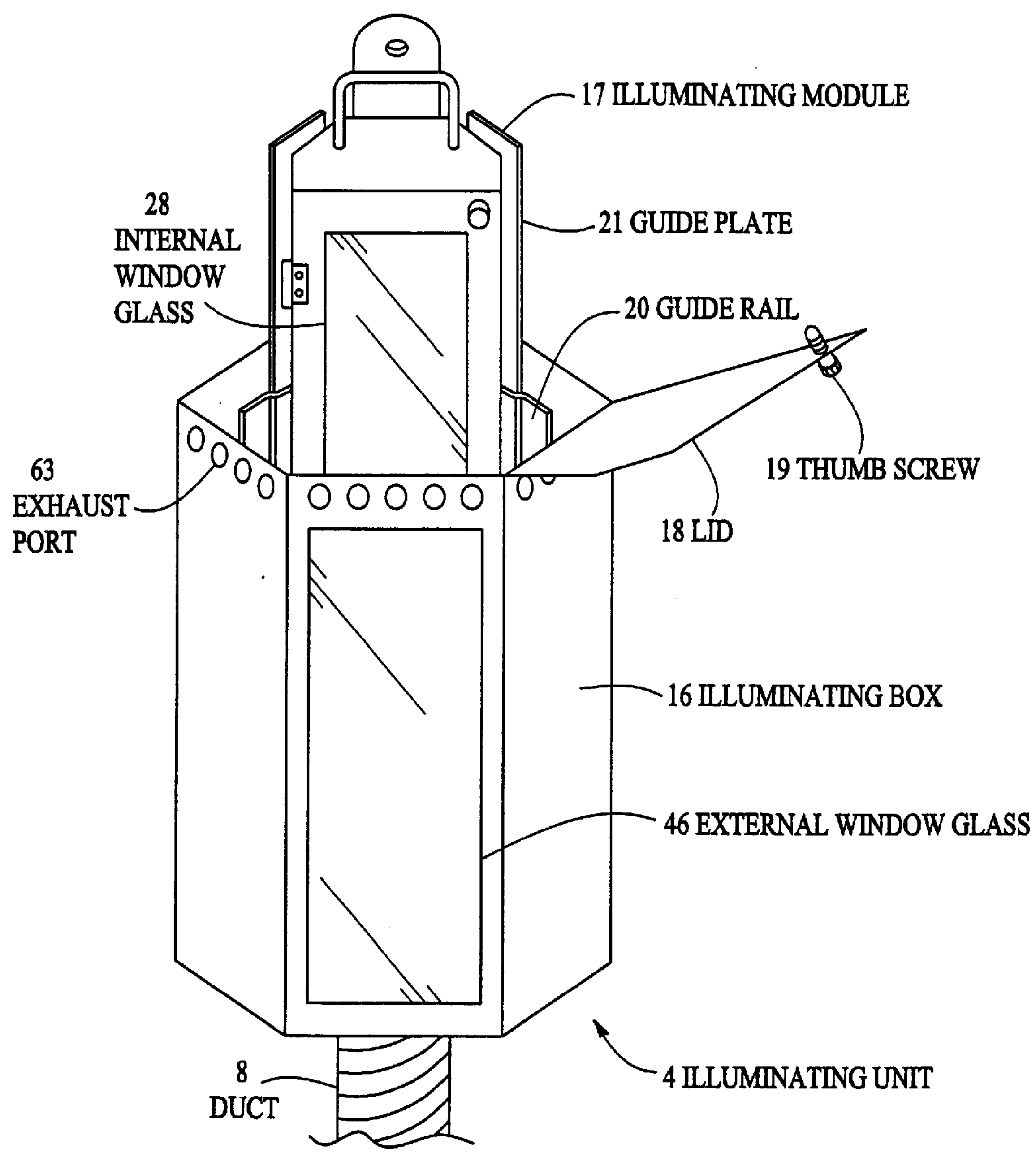
FIG. 2 is a perspective view showing a construction of an illuminating unit in FIG. 1.

Next, the construction of the illuminating units 4 will be described with reference to FIG. 2.

The illuminating unit 4 comprises an illuminating module 17 and an illuminating box 16.

Air flows into the illuminating box 16 through the air feed unit 7 and a duct 8 shown in FIG. 1.

The construction of the illuminating module in FIG. 2 will be explained in detail with reference to FIG. 3.

Figure 3:
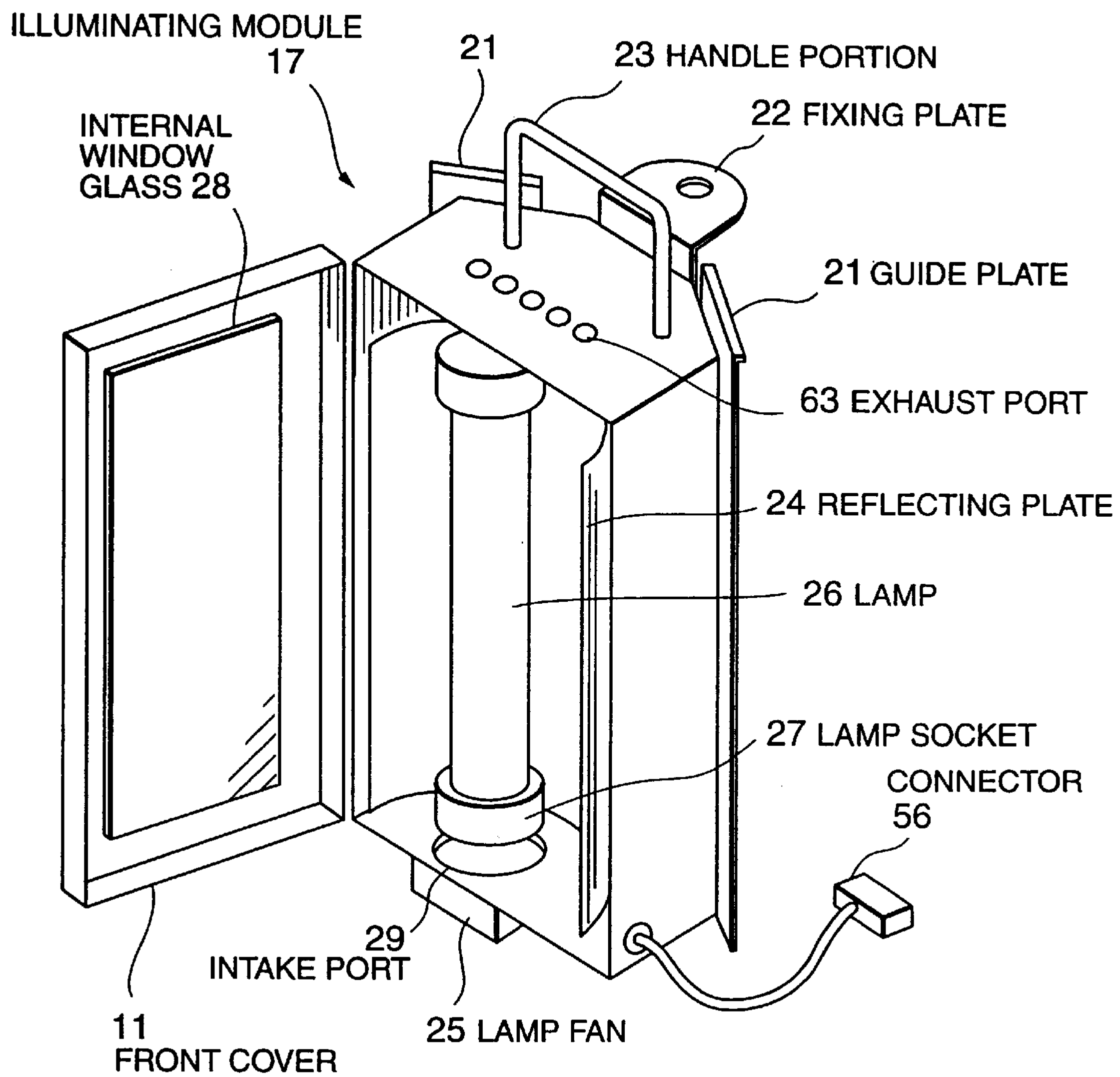
FIG. 3 is a perspective view showing a construction of an illuminating module in FIG. 2.

Referring to FIG. 3, the illuminating module 17 comprises a lamp 26 (such as a sodium lamp and a metal halide lamp); a lamp socket 27; a reflecting plate 24; a lamp fan 25; an internal window glass 28; exhaust port 63 a handle portion 23; a guide plate 21; and a fixing plate 22. The reflecting plate 24 is formed in a shape to direct illuminating light to the image pickup field 14. The lamp fan 25 cools the lamp 26 and atmosphere in the illuminating module 17 and a surface of the internal window glass 28.

The internal window glass 28 is made up of a heat ray absorbing glass, and this transmittance of a visible wavelength is partly changed so that the light distributing characteristics are made uniform. It is exemplified that the glass at the center portion is worked so as to have a rubbed glass form because the illuminance at the glass center portion is ordinarily increased, thereby dropping the transmittance.

The heat ray absorbing glass is subjected to an infrared cut coating process, so that it has a characteristic for increasing a contrast of a character written by ink of a ball-point pen, etc. which is reflected by near-infrared light.

Figure 4:
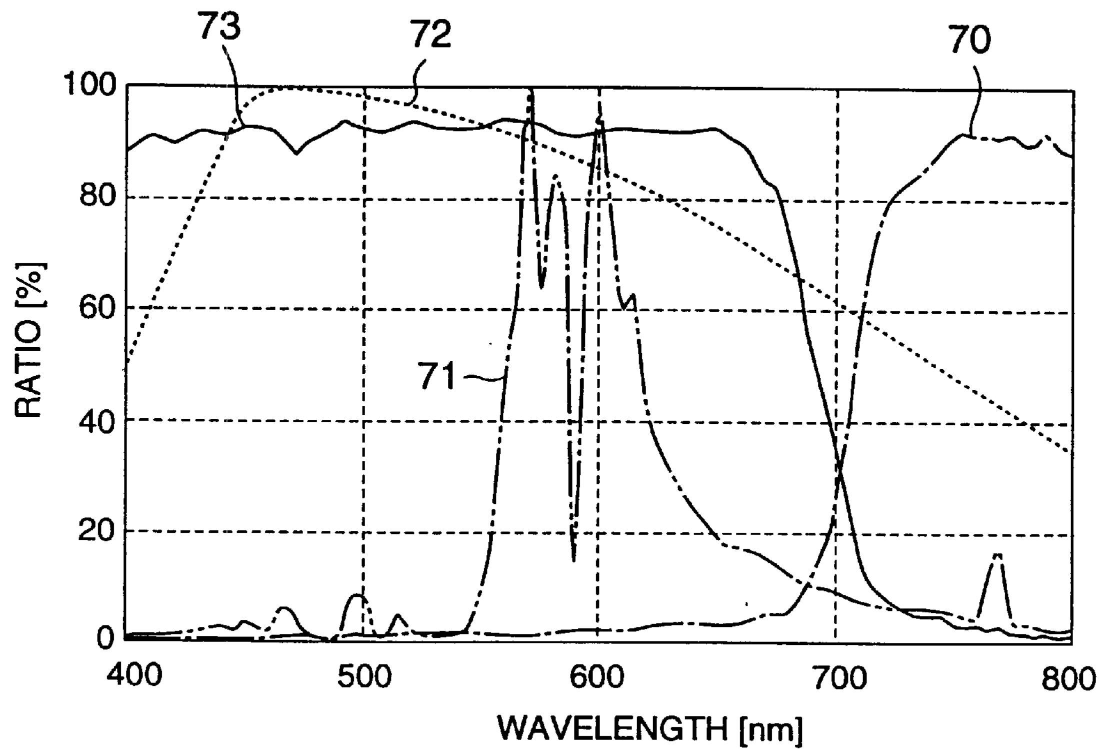
FIG. 4 is a diagram showing spectral characteristics of an ink reflection, a light-emitting intensity and CCD sensitivity.

Referring to FIG. 4, with respect to ink of a ball-point pen used frequently in writing an address of the mail item, an ink reflecting characteristic 70 indicative of a ratio of reflecting light to incident light shows a reflectance which is raised from a near point of 700 nm. A light-emitting intensity characteristic 71 of the sodium lamp shows a measure of intensity near 700 nm to 800 nm, and a CCD sensitivity characteristic 72 also shows a measure of sensitivity near 700 to 800 nm. Therefore, a CCD output exists in this wavelength area. Note that the light-emitting intensity characteristic 71 of the sodium lamp indicates a ratio of a light-emitting intensity of a wavelength component to a light-emitting intensity of a wavelength whose light-emitting intensity is maximum in case thereof the ratio is 100%. When there is no infrared cut coating, the reflecting level of the character written by the ball-point pen is made close to a reflecting level of the sheet surface. This results in decreasing a contrast and making it difficult to obtain a clear pattern, and finally has adverse effects upon character recognition. To solve the problem, according to the image input apparatus of the present application, a heat ray absorbing characteristic 73 is implemented by coating having a characteristic which is matched to the ink reflecting characteristic 70 of the ball-point pen and the most suitable for picking up a character image on the basis of an experience rule by the corporation concerned, as shown in FIG. 4. That is, a wavelength for which the transmittance falls is set to 700 nm. If the rising wavelength is set to a side of a wavelength longer than 700 nm, the character contrast decreases and character quality lessens. If the rising wavelength is set to a side of a wavelength shorter than 700 nm, an optical energy made incident to the CCD is decreased and an S/N ratio of an image signal drops, thereby diminishing the image quality and adversely influencing character reading characteristics.

The handle portion 23 is a portion for holding the illuminating module 17 when pulling out it from the illuminating box 16 for purpose of lamp exchange, and makes the exchanging operation simple. The guide plate 21 can be simply detached by being carried along a guide rail 20 provided in the illuminating box 16 as shown in FIG. 2, and also assures positioning precision of the irradiating angle. The fixing plate 22 is tightened together by a thumb screw 19 which is half fixed to a lid 18 of the illuminating box 16 shown in FIG. 2. As mentioned above, the detachable illuminating module enables the lamp to be exchanged speedily.

Figure 5:
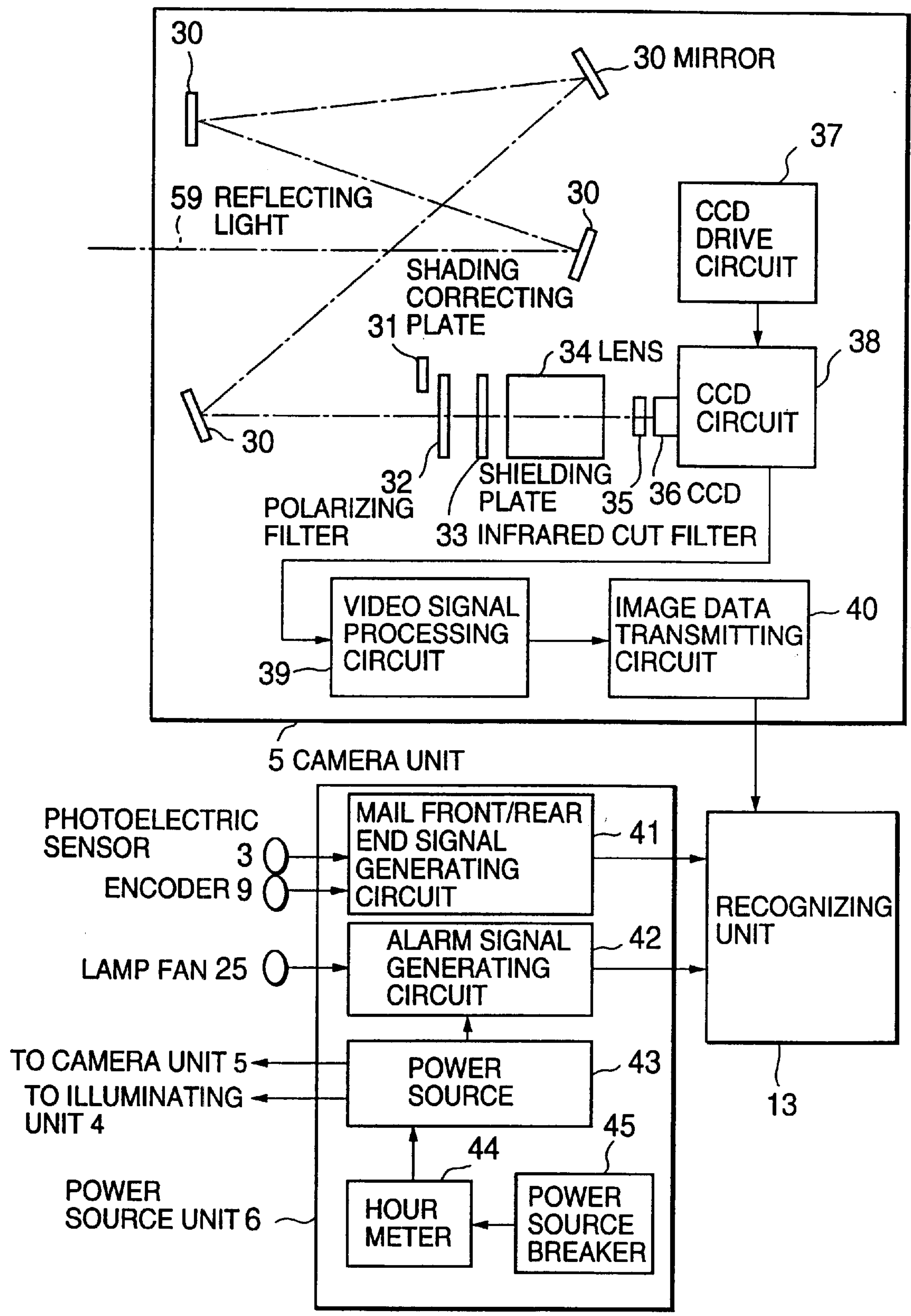
FIG. 5 is a block diagram showing an outline of a circuit construction in FIG. 1.

Referring to FIG. 5, the description turns to the circuit construction according to the first embodiment of the present invention.

As shown in FIG. 5, a camera unit 5 comprises: a CCD 36 of a linear array type which receives an image formed by converging a reflecting light 59 from a surface of the mail item 2 by a lens 34; a CCD circuit 38 for converting light into an electric signal; a CCD drive circuit 37 for generating a CCD drive signal; a video signal processing circuit 39 for amplifying the electric signal from the CCD circuit 38, normalizing a signal level, and digitally converting the signal; and an image data transmitting circuit 40 for parallel/serial converting a video signal, converting the signal into an optical signal, and transmitting the converted signal to the outside.

The power source unit 6 comprises: a mail front/rear end signal generating circuit 41 for delaying a signal of the photoelectric sensor 3 for a predetermined time in accordance with the pulse generated by the rotary encoder 9 and transmitting the delayed signal to the outside; an alarm signal generating circuit 42 for outputting various alarm signals to the outside; a power source 43; an hour meter 44 for estimating and displaying an energizing time for purpose of maintenance; and a power source breaker 45.

The operation of the first embodiment will be now described.

Referring to FIG. 1, the mail item 2 is conveyed at a predetermined speed of 1.5 m/s by the conveyor belt 1. A timing signal to capture an image is notified to a recognizing unit 13 via the power source unit 6 by a signal of the photoelectric sensor 3 of a transmission type which is set in front of the image pickup field 14.

The mail item 2 passing through the photoelectric sensor 3 reaches the image pickup field 14. An image of the mail item 2 is picked-up by the camera unit 5 when passing through the camera filed 14 as follows. The two illuminating units 4 illuminates a field range during a necessary depth of field (such as 50 mm) with a uniform light-distribution, holding a predetermined illuminance.

The illuminating units 4 are mounted to illuminate the mail item 3 at an angle of about 45°, sandwiching the camera optical axis 15. Since the camera optical axis 15 is perpendicular to the mail item, it is possible to suppress the occurrence of a shade due to unevenness of a sheet surface and regular reflection by a vinyl envelop. There is also small geometric distortion in the image due to the unevenness.

Reflecting light from the surface of the mail item 2 is reflected by four mirrors 30 shown in FIG. 5 and, thereafter, an image is formed by the lens 34 onto the CCD 36. The mirrors 30 are used so as to ensure a light path length in a limited space as much as possible and reduce variation in magnification of the image in accordance with variation in thickness of the flat mail. According to the present embodiment, the mirrors 30 are disposed so that the light path intersects and the light path is returned four times, thereby saving the space. The magnification of the lens 34 is selected to capture an image of the mail item 2 by a resolution of 8.5 lines/mm in the scan direction and a field of 300 mm. Therefore, the number of pixels used actually by the CCD is 2550 (which is obtained by <8.5 (pixels/mm) *300 mm>. The CCD 36 converts, into an electric signal, light which is formed into an image by the lens 34.

With regard to the CCD for purpose of low costs, there is used a CCD having 5 k pixels for general-purpose use, which is employed for a low end scanner, and further utilizes only 2550 pixels among the 5 k pixels. In recent years, the number of CCD pixels tends to be increased, and a CCD of 5 k pixels or more is used mainly at present. Scale merit of production also makes those CCDs inexpensive. However, an upper limit of a data rate is about 40 MHz. As a consequence, an exposing time becomes longer proportionally to the number of pixels, so that the resolution in the conveying direction 209 drops. In case of, e.g., a uPD35H71 as a CCD for general-purpose use produced by NEC corporation, the number of valid pixels is 5 k bits and the data rate is 40 MHz. As a result, according to a normal driving method (of starting to expose a next line after transferring all of the valid pixels to the outside), the CCD exposing time is 128 $\mu$s [=5 k/40 (MHz)] at the minimum level. In case of the conveying speed of 1.5 (m/s), the resolution in the conveying direction is 5.2 lines/mm [=1/<1.5 (m/s)*128 ($\mu$s)>] at the maximum level and this does not suffice for the scan direction resolution.

According to the image input apparatus of the present invention, the exposing time is made short and the resolution in the conveying direction 209 is increased. However, one simply shortens the exposing time, the exposing affects successively the previously exposed pixels, since transfer of the previously exposed pixel data to the external is still under way. This result deteriorates image quality. Thus, a range except for the actual used pixels (2550 pixels) is light-shielded by a shielding plate 35 to prevent the unused pixels from being exposed. That is, according to the present invention, one is able to use an inexpensive CCD for general-use purpose by masking a portion for which no CCD photosensor is utilized and using only a necessary range.

Herein, attention should be given to a point that there is a fine space between the shielding plate 35 and the CCD 36 and, therefore, the photosensor under an edge portion of the shielding plate 35 is also exposed slightly by light leakage due to light diffraction at the edge portion of the shielding plate 35. This problem is avoided by transferring image data including even a part of the unused pixels in addition to the actual used pixels. According to the present embodiment, since the resolution is 8.5 lines/mm, the exposing time is about 78.43 $\mu$s [=<1/8.5 (lines/mm)>/1.5 (m/s)]. Thus, the number of pixels is equal to about 3137 (=78.43 43 $\mu$s/25 ns). The remaining 587 pixels are used as vacant transfer pixels for light-leakage countermeasure, excluding 2550 valid pixels. As a consequence of an experiment, the number of pixels due to the light leakage is almost equal to 100 and there is a sufficient margin, thereby having no influence to image quality.

Figure 6:
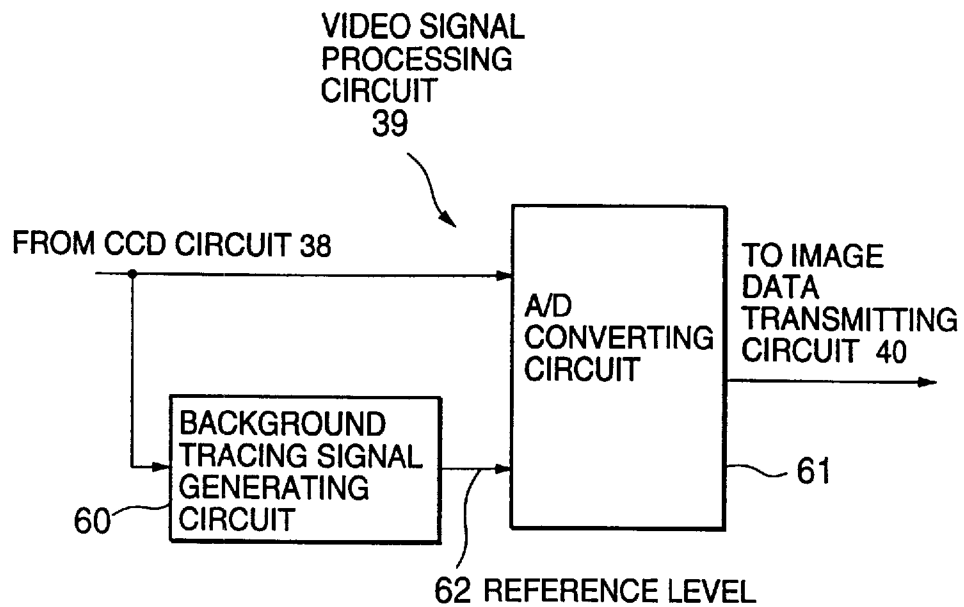
FIG. 6 is a block diagram showing a construction of a video signal processing circuit in FIG. 5.

The video signal processing circuit 39 A/D-converts a video signal outputted from the CCD circuit 38. As shown in FIG. 6, a reference level 62 to digitize the signal by the A/D converting circuit 61 utilizes an output signal of a background tracing signal generating circuit 60 to generate an envelop of a sheet surface level. Thus, illuminating blur and luminous blur on the sheet surface caused by lens shading are corrected, thereby obtaining an image having a uniform luminosity.

The camera unit 5 is therein provided with: a shading correcting plate 31; the mirrors 30; a polarizing filter 32; an infrared cut filter 33; and a shielding plate 35 for shielding light of the unused pixels of the CCD 36.

Referring to FIG. 5, there are set in front of the lens 34: the shading correcting plate 31; the polarizing filter 32; and the infrared cut filter 33. The shading correcting plate 31 is, for example, semicircular. A light quantity of light beams at the center is cut, and to thereby correct the shading (luminous blur) caused by the characteristics of the lens itself. The infrared cut filter 33 cuts near infrared light and infrared light and raises the contrast of a character written by ink of the ball-point pen, etc. which is reflected by the near infrared light similarly to the infrared light cut coating which is subjected to the heat ray absorbing glass. Note that no infrared cut filter 33 may be employed if the infrared cut coating is effected to the heat ray absorbing glass so as to increase the contrast of the character written by ink of the ball-point pen etc. which is reflected by the near infrared light.

The polarizing filter 32 is utilized to remove regular reflecting light from the mail item which is covered with a package material such as vinyl for which it is easy to cause mirror reflection, in accordance with a well-known principle.

The illuminating apparatus used for the image input apparatus according to the present application employs a lamp having a large power because it is necessary to illuminate a wide range of volume by a high illuminance. In case of the sodium lamp, two lamps of 150 W are necessary. Thus, there occurs a problem that heat dissipation leads to high temperature of the window glass. For example, the conveyance of the mail item makes dusts and foreign matters (such as a vinyl piece and a rubber band piece) scattered near the image input apparatus, thereby causing burning if those adhere to the window glass having high temperature. This burning makes the light distribution of the illuminating light disturbed. The image quality is degraded, thereby influencing the recognizing performance adversely. To avoid such a situation, a frequent cleaning operation is necessary and the maintenance performance is reduced. To avoid the aforementioned problem, the image input apparatus of the present application has the following configuration.

Figure 8:
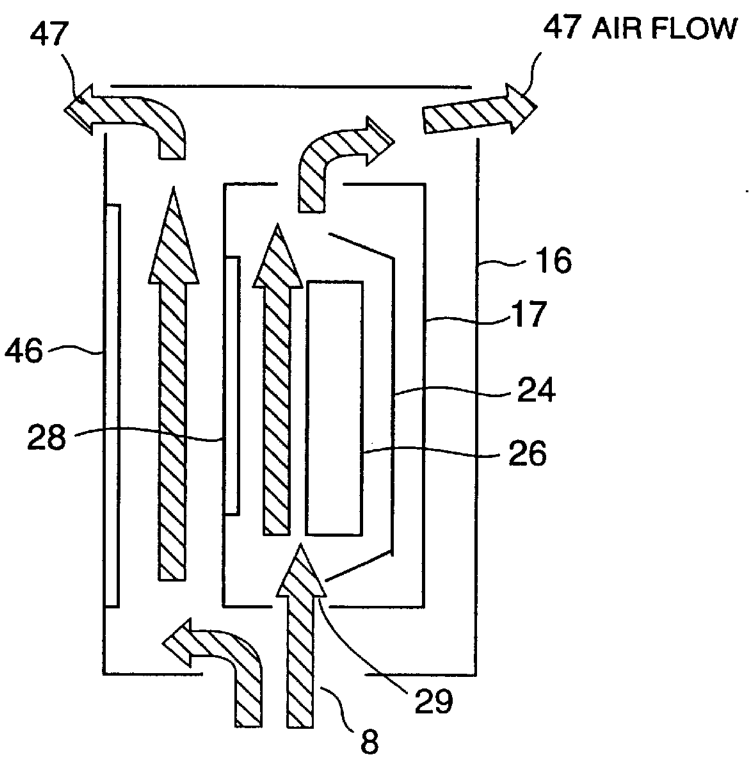
FIG. 8 is a diagram showing an air flow in the illuminating unit according to the present invention.

A heat ray absorbing glass is adopted as the internal window glass 28 of the illuminating module 17 so as to decrease the quantity of heat dissipated by the lamp 26 in the illuminating unit 4. Although increasing the temperature of atmosphere between the illuminating module 17 and the illuminating box 16 and the inside of the illuminating module 17 as well as increasing the temperature of the internal window glass 28 itself, the increase in temperature is suppressed by generating an air flow 47, as shown in FIG. 8. On the other hand, the heat ray transmitting glass is adopted as the external window glass 46. Thus, the temperature of the glass itself is not increased. If the internal window glass 28 absorbs a large part of the heat rays and the air flow 47 causes the atmosphere temperature and the internal window glass temperature to be decreased almost up to the room temperature, the temperature of the external window glass 46 is held at the room temperature and there is also little heat-ray dissipation, thus avoiding the phenomenon that the heat burns the deposit. Accordingly, one is able lengthen a cycle for maintenance such as window glass cleaning and improving the maintenance performance. The principle of the heat dissipating system will be explained with reference to the drawing.

Figure 9:
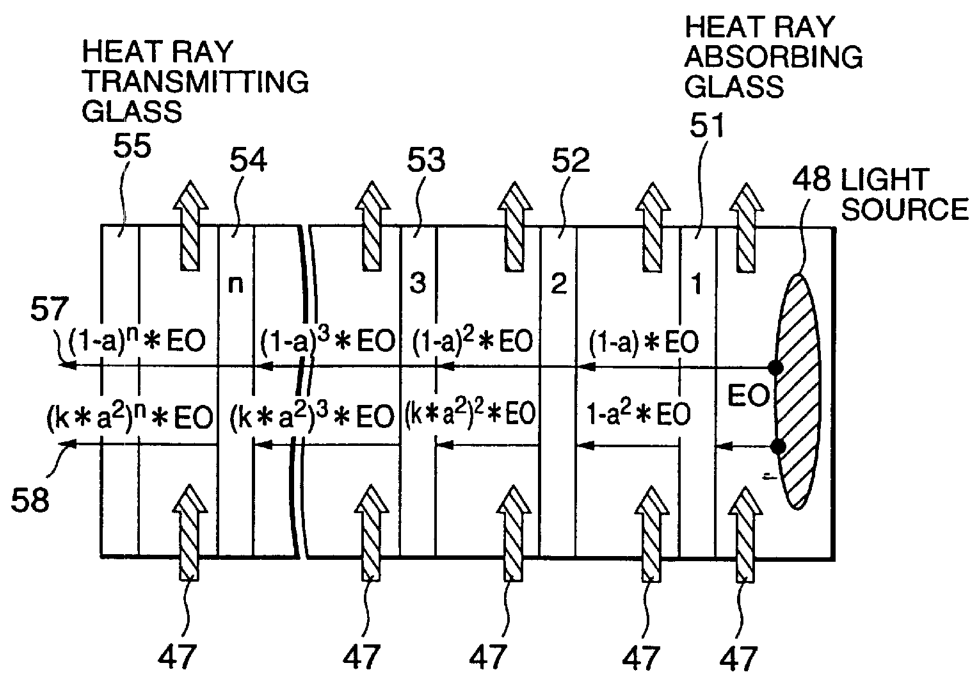
FIG. 9 is a diagram showing a model of a heat-dissipating system according to the present invention.

FIG. 9 illustrates a module for the heat dissipating system. Referring to FIG. 9, heat ray absorbing glasses 51 to 54 as a first glass to an n-th glass are inserted between the light source 48 and the heat ray transmitting glass 55 at proper intervals. Air is the medium of space. Air having a room temperature Tc flows from the downward direction to the upward direction in the space partitioned by the heat ray absorbing glass 51. The temperature of the light source 48 is equal to T0 (>Tc).

As stated above, it is the object of the present heat dissipating system to prevent the dusts and vinyl, etc. touching the external window glass (46 or 55) from being burned by the heat. A simple model of the burning as a premise of the present application will be indicated in FIG. 7.

Figure 7:
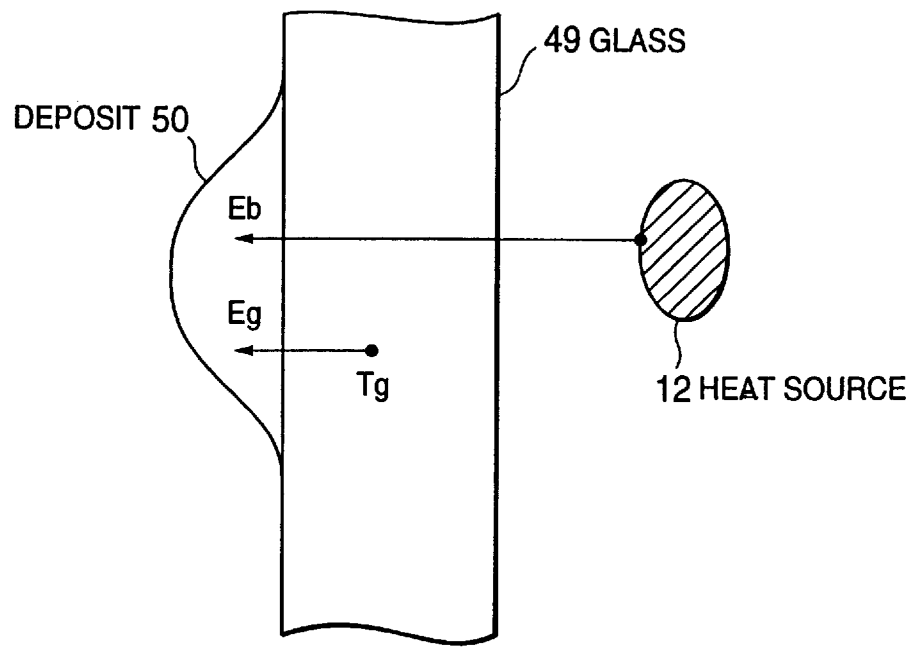
FIG. 7 is a diagram showing a model to burn a deposit to a glass according to the present invention.

Referring to FIG. 7, a deposit 50 receives: a heat dissipating energy Eg, which is generated by a temperature Tg of the glass in accordance with a Stefan-Boltzmann's law as a well-known fact and determined by the following formula; and a heat dissipating energy Eb from a heat source 12, which is transmitted through a glass 49.

$$Eg=e*r*Tg^4(W/m^2)$$

r: well-known constant e: emissivity of heat source

The dissipating energy of (Eg+Eb) and heat conduction of the glass raise the temperature of deposit 50 in accordance with the well-known fact, and the deposit 50 adheres and fixes to a surface of the glass 49. Therefore, it is necessary to suppress the increase in glass temperature and reduce the quantity of heat dissipating energy. Based on this, the principle of the present embodiment will be now described hereinbelow.

Herein, the temperature of the glass is increased by: (1) heat dissipation; (2) heat conduction; and (3) convection current, in accordance with the well-known fact. However, by reasons of extremely small heat conductivity of air and the employment of the forced air-cooling means, it is assumed that a main factor of the temperature increase is (1) heat dissipation in this model.

Referring to FIG. 9. the heat ray absorbing glass 51 as a first glass receives a heat dissipating energy E0, which is generated by the temperature T0 of the light source 48 in accordance with the Stefan-Boltzmann's law as the well-known fact.

$$E\mathbf{0}=e*r*T\mathbf{0}^4(W/m^2)$$

r: well-known constant e: emissivity of heat source

Accordingly, the heat ray absorbing glass 51 as a first glass obtains a temperature T1 (<T0), at which the balance is kept between the temperature increase by the heat dissipating energy E0 and the temperature decrease by air-cooling. Next, the heat ray absorbing glass 52 as a second glass receives a heat dissipating energy Es1, which is obtained by superposing a heat dissipating energy ($k*a^2*E\mathbf{0}$) by the temperature T1 of the heat ray absorbing glass 51 as a first glass and a heat dissipating energy $(1-a)*E\mathbf{0}$ from the light source.

$$Es1=(1-a)*E\mathbf{0}+k*a^2*E\mathbf{0}(W/m^2)$$

a: absorptance and emissivity of glass k: decreasing rate by air-cooling where, assuming that the reflectance of glass is equal to 0 and the absorptance is equal to the emissivity.

Thus, the heat ray absorbing glass 52 as a second glass absorbs the heat dissipating energy Es1, so that a temperature of T2 (<T1) is obtained. After that, the similar operation is repeated up to the heat ray absorbing glass 54 as an n-th glass. A final heat ray transmitting glass 55 receives a heat dissipating energy Esn obtained by adding heat dissipating components 58 of the glasses to heat dissipating components 57 from the heat source 48, and the received heat dissipating energy Esn is continuously transmitted to the outside.

$$Esn=(1-a)^n*E\mathbf{0}+(k*a^2)^n*E\mathbf{0}(W/m^2)$$

$$(Esn/E\mathbf{0})=(1-a)^n+(k*a^2)^n$$

Generally, since 0<a<1 and 0<k<1, $$(Esn/E\mathbf{0})<1$$

As explained above, it is possible to obtain an effect to diminish the heat dissipating energy to dissipate the heat to the outside. The temperature of the heat ray transmitting glass 55 is not increased by the heat dissipating energy Esn by way of absorbing no heat ray.

The present embodiment corresponds to a case of n=1 in the above discussion. Under the experiment example, it is confirmed that the temperature of the external window glass 46 is reduced to about 50 C.° in the case where the internal window glass 28 has a temperature of about 100 C.°, if lighting on a sodium lamp of 150 W at a room temperature.

The illuminating module 17 has a simply detachable structure. When exchanging the lamp, the thumb screw 19 is detached and the lid 18 is opened. The illuminating module 17 and the main body are tightened together by the thumb screw 19 and, therefore, there is no screws except for the thumb screw 19. A connector 56 is detached and the handle portion 23 is pulled up. Successively, a spare illuminating module is mounted in accordance with the sequence opposite to the foregoing. In this instance, the guide plate 21 is allowed to travel along the guide rail 20 of the illuminating box 16 and, thus, simply accommodated to a specified position with accuracy. The irradiating angle is determined precisely and the image quality is stabilized and held. After connecting the connector 56, so long as closing the lid 18 and tightening the thumb screw 19, the exchange of lamp is finished. According to this module exchanging method, it is able to suppress a system down time of the mail sorter to the minimum level. The lamp is exchanged by detaching two thumb screws (not shown) and opening the front cover 11 after the lamp 26 is fully cooled. This illuminating module is kept by way of next module exchange.

It is to be noted that although one example is indicated with regard to the aforementioned values of the field, resolution, and conveying speed, etc., the present invention is not restricted by this example.

Next, the second embodiment of the present invention will be now described in detail with reference to the drawings.

The present embodiment is constructed by integrating the camera unit 5, illuminating units 4, air feed unit 7, and power source unit 6 in the first embodiment.

Figure 10:
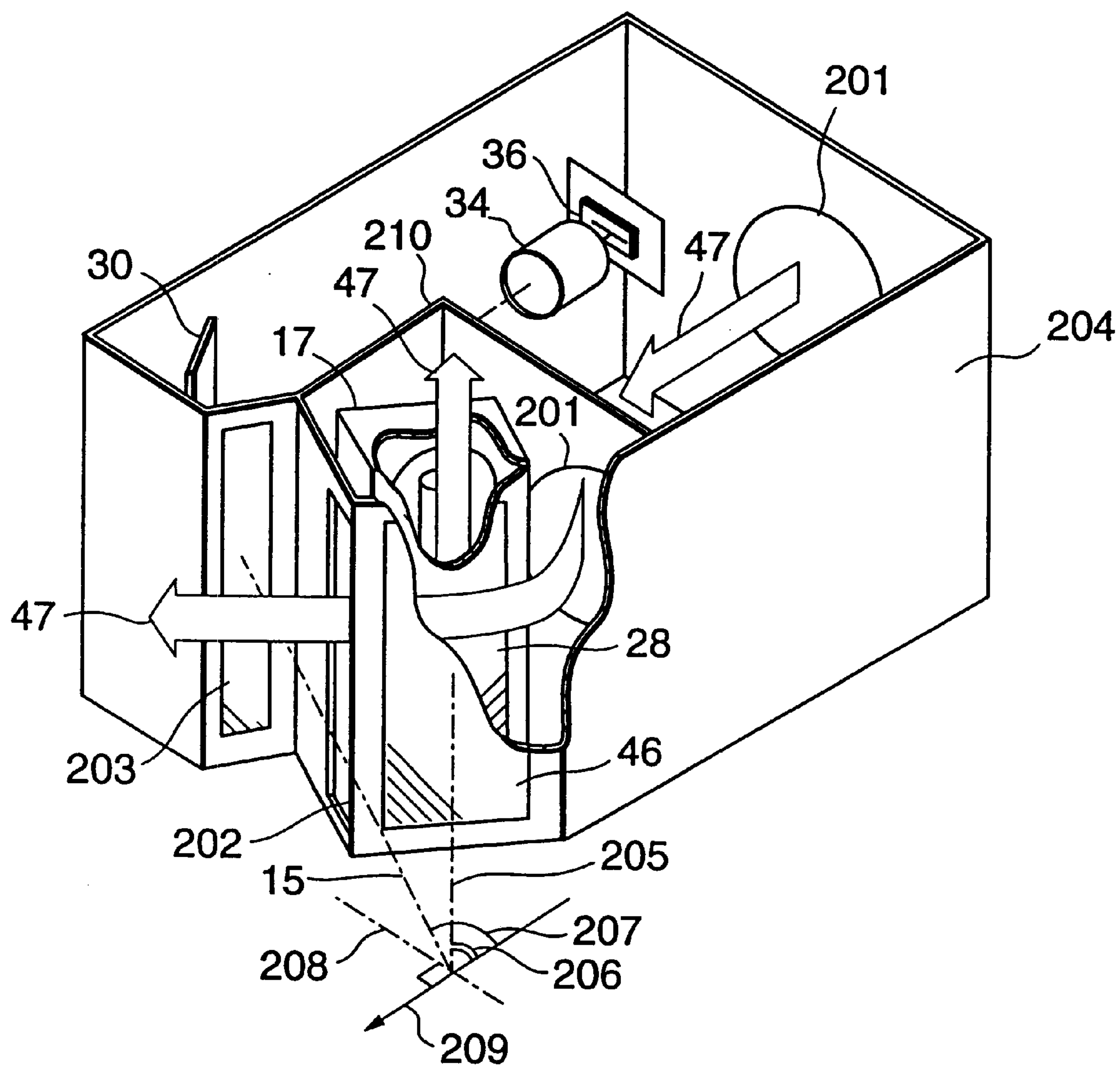
FIG. 10 is a perspective view showing a construction of an integrated unit according to a second embodiment of the present invention.

Referring to FIG. 10, there are built in an integrated casing 204: the illuminating module 17, camera unit 5, and power source unit 6. The illuminating module 17 is accommodated in a space partitioned by a partition 210. FIG. 10 shows only the mirror 30, lens 34, and CCD 36 of the camera unit 5, and does not show other components of the camera unit 5 and the power source 6.

The operation of the second embodiment will be expressed with reference to FIG. 10. An air-cooling fan 201 generates the air flow 47. The air flow 47 is exhausted from an exhaust port 202, via the partition 210 and a space between the internal window glass 28 and the external window glass 46. The air flow 47 is generated by the lamp fan 25 mounted to the downside of the illuminating module 17 therein. According to the principle similar to that of the first embodiment, the air flow generation makes it possible to avoid inconvenience such as burning of the deposit adhered to the external window glass.

According to the present embodiment, an acute angle is formed between the illuminating light optical axis 205 and the camera optical axis 15, for the conveying direction 209. An angle 206 formed between the illuminating light optical axis 205 and the conveying direction 209 is smaller than an angle 207 formed between the camera optical axis 15 and the conveying direction 209. This makes it difficult to occur a defective image such as halation due to the regular reflection of an mail item packaged by a package material such as vinyl having a quality which is apt to cause mirror reflection, and a stable image is obtained.

The third embodiment of the present invention will be now described with reference to the drawings.

The present embodiment has a construction such that a focus control module is added to that of first embodiment or second embodiment.

The focus control module comprises: a thickness sensor 304 to measure the thickness of a mail item; a plane glass block 301 for correction; a drive unit 302 for driving the plane glass block 301 for correction; and a control unit 303 to control the drive unit 302.

The operation of the third embodiment will be now described hereinbelow.

The present embodiment can correspond to a thicker mail item.

Figure 11:
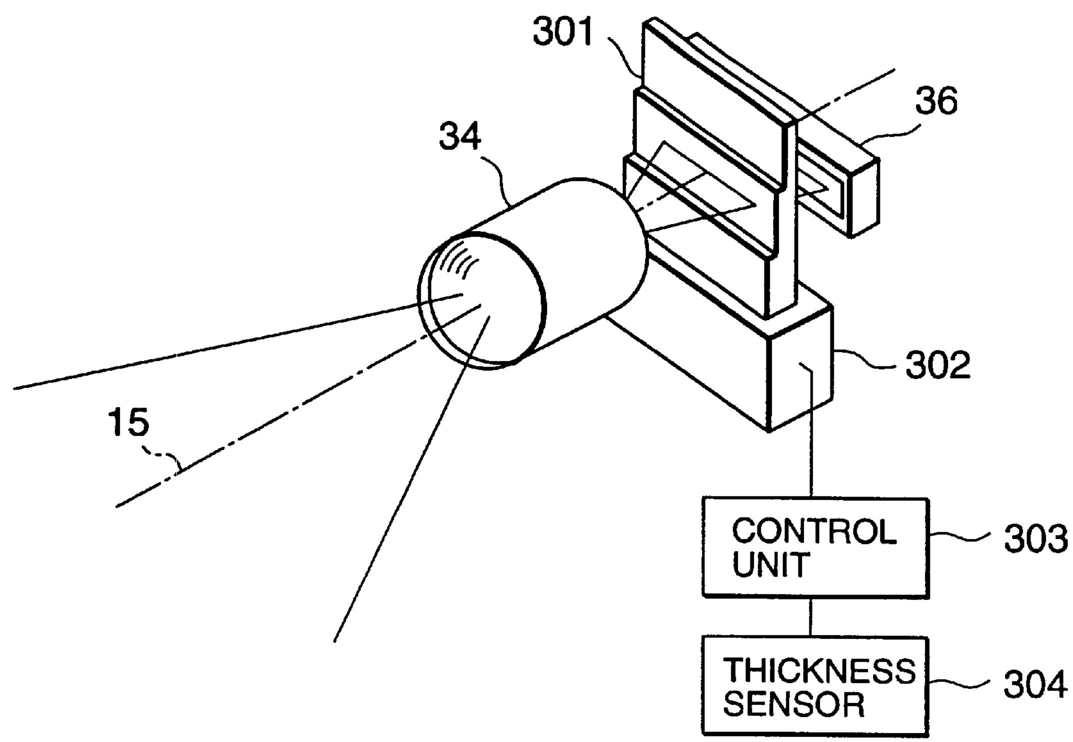
FIG. 11 is an external view of a focus control module according to a third embodiment of the present invention.

The present embodiment is embodied by applying a principle, which will be discussed hereinafter, and the operation will be expressed with reference to FIG. 11.

A thickness Dm of a mail item is measured by the thickness sensor 304 provided in a conveying passage, and the resultant thickness is noticed to the control unit 303. The control unit 303 calculates a thickness Dg of the correcting glass necessary for the thickness Dm. The control unit 303 notifies the drive unit 302 of a control signal to select a glass whose thickness is the closest to the calculated thickness Dg. The drive unit 302 drives the glass block 301 for correction and positions it so that the selected thickness glass is inserted in a light path. This construction makes a depth of field deep and, therefore, widens a range of the thickness of the mail item which can be captured clearly.

According to the present embodiment, the glass block 301 for correction indicates the construction in which three plane glasses having different thicknesses are aligned rectangularly. Each plane glass has a size which does not obstruct the light beams. In this case, the control unit 303 selects a thickness which is the closest to the correcting value as a calculated result, among the three glasses.

Figure 12:
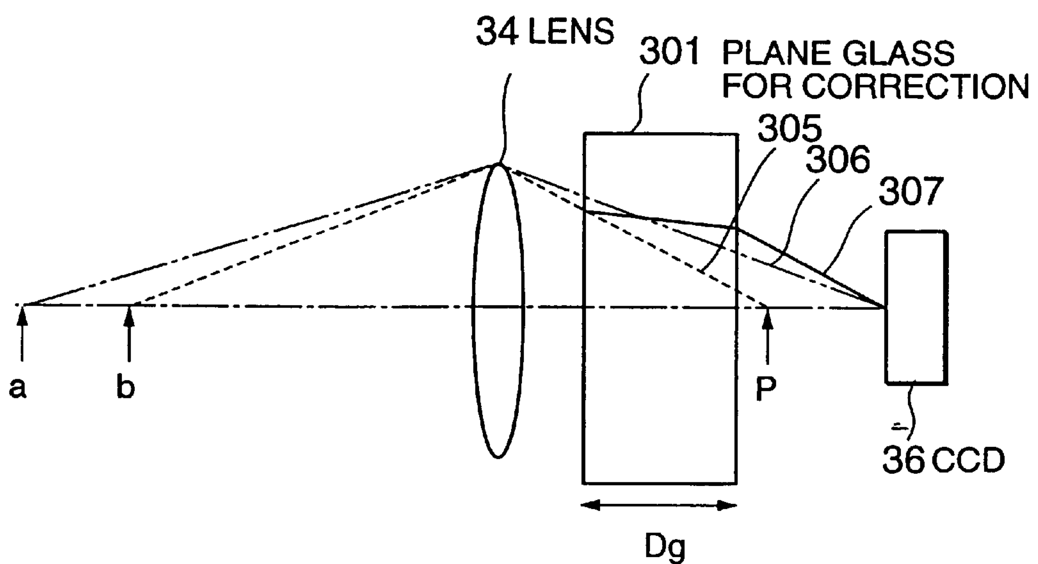
FIG. 12 is a diagram showing a principle of a focus correction according to the third embodiment of the present invention.

The next description turns to a principle such that a plane glass having a different glass is selected and inserted into the light path, thereby enabling the depth of field of camera deep, with reference to FIG. 12. Referring to FIG. 12, the position of the lens 34 is controlled so that an object at a position b forms an image on the CCD 36 when there is no correcting glass 301. If the position of the object goes away to a position a, a focus position is located at a position P on an image surface and the image on the CCD 36 is out of focus. If the correcting glass 301 having the proper thickness Dg is inserted in the light path between the lens 34 and the CCD 36 in the foregoing state, light refraction enables the light path to be lengthened, as shown in FIG. 12. Accordingly, the thickness Dg is properly selected, and the image can be formed on the CCD 36.

When a thickness change quantity of a mail item (object) is equal to Dm, it is able to determine the thickness Dg of the correcting glass necessary for controlling the change quantity as follows.

It is capable of obtaining the following formula of a focus deviating quantity e in accordance with the thickness change of the mail item, based on a fundamental formula of lens.

$$e=<s*f/(s-f)>-<(s+Dm)*f/(s-f+Dm)>$$

As shown in "Introduction to Image-forming Optics" written by Yoshiya MATSUI, published by Keigaku Shuppan, it is possible to obtain the thickness Dg to correct the focus deviating quantity e of the correcting glass by the following formula.

$$Dg=e/(1-1/n)$$

where, n: refractive index of plane glass f: focusing distance of lens s: distance between lens and object e: focus deviating quantity Based on this principle, the thickness Dg of the correcting glass necessary for the thickness Dm is calculated by the thickness Dm of the mail item which was measured, the glass of the thickness closest to the calculated thickness Dg is selected, and the selected glass is inserted into the light path.

By selecting the plane glasses having different thicknesses and inserting them into the light path, it is possible to deepen the depth of field, widen the thickness range of the mail item captured clearly, increase a target quantity of an automatic sorting process, and saving labor to sort mail items.

While this invention has been described with reference to illustrative embodiments, this description is not intended to be construed in a limiting sense. Various modifications of the illustrative embodiments, as well as other embodiments of the invention, will be apparent to persons skilled in the art upon reference to this description. It is, therefore, contemplated that the appended claims will cover any such modifications or embodiments as fall within the true scope of the invention.

What is claimed is:

1. An image input apparatus comprising:

conveying means for moving an object in a predetermined direction;

two illuminating means for illuminating said object, respectively comprising a light source for irradiating light to said object, an internal window glass serving as a heat ray absorbing glass through which said light from said light source is transmitted, and an outermost window glass serving as a heat ray transmitting glass through which a light transmitted through said internal window glass is transmitted;

image pickup means for picking up an image of said object illuminated by said two illuminating means, having an image pickup field positioned between said two illuminating means; and air cooling means for generating an air flow to forceably cool a front surface of said internal window glass and a rear surface thereof further comprising a casing having said outermost window glass; and an accommodating box which houses said internal window glass and said light source, separable and detachable from said casing.

2. An image input apparatus comprising:

conveying means for moving an object in a predetermined direction;

single illuminating means for illuminating said object, comprising a light source for irradiating light to said object moved in the predetermined direction by said conveying means, an internal window glass serving as a heat ray absorbing glass through which the light from said light source is transmitted, and an outermost window glass serving as a heat ray transmitting glass through which light transmitted through said internal window glass is transmitted;

image pickup means for picking up an image of said object to which said light from said illuminating means is irradiated in an image pickup field of said image pickup means;

air cooling means for generating an air flow to forceably cool a front surface of said internal window glass and a rear surface thereof; and wherein an acute angle is formed between an optical axis of said image pickup means and said conveying direction, and an angle formed between an optical axis of said illuminating means and said conveying direction is smaller than an angle formed between the optical axis of said image pickup means and said conveying direction.

3. An image input apparatus comprising:

conveying means for moving an object in a predetermined direction;

single illuminating means for illuminating said object, comprising a light source for irradiating light to said object moved in the predetermined direction by said conveying means, an internal window glass serving as a heat ray absorbing glass through which the light from said light source is transmitted, and an outermost window glass serving as a heat ray transmitting glass through which light transmitted through said internal window glass is transmitted;

image pickup means for picking up an image of said object to which said light from said illuminating means is irradiated in an image pickup field of said image pickup means;

air cooling means for generating an air flow to forcibly cool a front surface of said internal window glass and a rear surface thereof; and wherein an acute angle is formed between an optical axis of said image pickup means and said conveying direction, and an angle formed between an optical axis of said illuminating means and said conveying direction is larger than an angle formed between the optical axis of said image pickup means and said conveying direction.

4. An image input apparatus comprising:

conveying means for moving an object in a predetermined direction;

two illuminating means for illuminating said object, respectively comprising a light source for irradiating light to said object, an internal window glass serving as a heat ray absorbing glass through which said light from said light source is transmitted, and an outermost window glass serving as a heat ray transmitting glass through which a light transmitted through said internal window glass is transmitted;

image pickup means for picking up an image of said object illuminated by said two illuminating means, having an image pickup field positioned between said two illuminating means; and air cooling means for generating an air flow to forceably cool a front surface of said internal window glass and a rear surface thereof;

wherein said image pickup means has image forming means, photoelectric converting means, video signal processing means, and image data transmitting means;

thickness measuring means for measuring a thickness of the object; and focus control means for changing a focus position of said image forming means in accordance with a measured result by said thickness measuring means;

wherein said focus control means comprises: a plane glass; drive means for matching said plane glass to the light path; and a control unit for controlling said drive means in accordance with the result of said thickness measuring means.

5. An apparatus according to claim 4, wherein said plane glass comprises two or more portions whose thicknesses are different.

6. An image input apparatus comprising:

conveying means for moving an object in a predetermined direction;

two illuminating means for illuminating said object, respectively comprising a light source for irradiating light to said object, an internal window glass serving as a heat ray absorbing glass through which said light from said light source is transmitted, and an outermost window glass serving as a heat ray transmitting glass through which a light transmitted through said internal window glass is transmitted;

image pickup means for picking up an image of said object illuminated by said two illuminating means, having an image pickup field positioned between said two illuminating means; and air cooling means for generating an air flow to forceably cool a front surface of said internal window glass and a rear surface thereof;

wherein said image pickup means comprise photoelectric covering means;

said photoelectric converting means comprises a linear array CCD (Charge Coupled Device) which is formed by linearly aligning light receiving elements, said light receiving elements including actual used elements for picking up the image of said object and unused elements; and said image pickup means further has shielding means for shielding a part of light of said linear array CCD to prevent the unused elements from being exposed.

7. An image input apparatus comprising:

conveying means for moving an object in a predetermined direction;

two illuminating means for illuminating said object, respectively comprising a light source for irradiating light to said object, an internal window glass serving as a heat ray absorbing glass through which said light from said light source is transmitted, and an outermost window glass serving as a heat ray transmitting glass through which a light transmitted through said internal window glass is transmitted;

image pickup means for picking up an image of said object illuminated by said two illuminating means, having an image pickup field positioned between said two illuminating means; and air cooling means for generating an air flow to forceably cool a front surface of said internal window glass and a rear surface thereof;

wherein said image pickup means has image forming means, photoelectric converting means, video signal processing means, and image data transmitting means;

wherein said video signal processing means has envelop detecting means to produce a reference signal representative of a surface level of said object and analog/digital converting means for generating a digital image signal by using said reference signal.

8. An image input apparatus comprising:

conveying means for moving an object in a predetermined direction;

two illuminating means for illuminating said object, respectively comprising a light source for irradiating light to said object, an internal window glass serving as a heat ray absorbing glass through which said light from said light source is transmitted, and an outermost window glass serving as a heat ray transmitting glass through which a light transmitted through said internal window glass is transmitted;

image pickup means for picking up an image of said object illuminated by said two illuminating means, having an image pickup field positioned between said two illuminating means; and air cooling means for generating an air flow to forceably cool a front surface of said internal window glass and a rear surface thereof;

wherein transmittance of the internal window glass of said illuminating means is reduced locally at a center position of said internal window glass.

* * * * *